United States Patent [19]

Michel

[11] Patent Number: 4,638,800

[45] Date of Patent: Jan. 27, 1987

[54] LASER BEAM SURGICAL SYSTEM

[75] Inventor: Thomas J. Michel, Miami, Fla.

[73] Assignee: Research Physics, Inc, Hollywood, Fla.

[21] Appl. No.: 699,933

[22] Filed: Feb. 8, 1985

[51] Int. Cl.$^4$ ............................................. A61B 17/36
[52] U.S. Cl. ................................................ 128/303.1
[58] Field of Search ............... 128/6, 303.1, 395–398; 350/607, 608, 611

[56] References Cited

U.S. PATENT DOCUMENTS

| | | | |
|---|---|---|---|
| 3,315,680 | 4/1967 | Silbertrust et al. | 128/395 |
| 3,659,613 | 5/1972 | Bredemeier | 128/395 |
| 3,804,095 | 4/1974 | Bredemeier | 128/303.1 |
| 3,818,902 | 6/1974 | Kinoshita et al. | 128/6 |
| 3,821,510 | 6/1974 | Muncheryan | 128/395 |
| 3,865,114 | 2/1975 | Sharon | 128/303.1 |
| 4,141,362 | 2/1979 | Wirster | 128/303.1 |
| 4,170,997 | 10/1979 | Pinnow et al. | 128/395 |
| 4,211,229 | 7/1980 | Wurster | 128/303.1 |
| 4,408,832 | 10/1983 | Hartman et al. | 350/607 |
| 4,420,222 | 12/1983 | Bret et al. | 350/607 |
| 4,425,026 | 1/1984 | Lien | 350/607 |
| 4,477,720 | 10/1984 | Pearson | 350/607 |
| 4,503,854 | 3/1985 | Jako | 128/303.1 |
| 4,548,482 | 10/1985 | Williams et al. | 350/607 |
| 4,550,240 | 10/1985 | Toida et al. | 128/303.1 |
| 4,556,057 | 12/1985 | Hiruma et al. | 128/303.1 |

FOREIGN PATENT DOCUMENTS

| | | | |
|---|---|---|---|
| 0058402 | 4/1984 | Japan | 350/607 |
| 2034961 | 3/1979 | United Kingdom | 128/6 |

Primary Examiner—Edward M. Coven
Assistant Examiner—Max F. Hindenburg
Attorney, Agent, or Firm—Michael Ebert

[57] ABSTRACT

A laser beam surgical system provided with a cannula insertable into a body passage leading to a surgical site. The cannula includes a rotatable inner tube whose inlet section has two input ports, one being in line with the tube axis and being coupled to a white light source, the other being at right angles to the axis and being coupled to a carbon dioxide laser projecting a collimated beam. Supported at a 45° angle within the inlet section is a pellicle that is permeable to the beam of white light impinging thereon and reflective to the laser beam whereby both are directed toward an outlet section at the other end of the tube. Supported within the outlet section at a 45° angle with respect to the tube axis is a normally planar reflective membrane which directs both beams through a lateral output port toward the surgical site which is illuminated by the white light. The geometric center of the membrane is coupled at its rear to a controllable actuator which forces the membrane to assume a concave form acting optically to bring the laser beam to a focus at a target surface on the surgical site.

13 Claims, 8 Drawing Figures

LASER BEAM SURGICAL SYSTEM

BACKGROUND OF INVENTION

1. Field of Invention:

This invention relates generally to laser beam systems for carrying out surgical procedures, and more particularly to a system using a carbon dioxide laser whose collimated laser beam is conducted through a cannula to an outlet section where the beam is directed by a reflective deformable membrane toward the surgical site, the membrane being controllable to assume a concave form which optically focuses the beam at a target surface on the site.

2. Status of the Art:

Throughout the course of modern surgery, the desideratum has always been for a technique by which one can execute the surgical procedure of interest in a manner optimizing operating room time and surgical effect while minimizing tissue trauma and bleeding as well as the period during which the patient is under anesthesia.

With the advent of miniaturized arthroscopic instruments, orthopaedic surgeons are now able to perform delicate operations in a relatively short time that were not heretofore feasible. An arthroscope is a cannula whose diameter is small enough to enter interstices between the bones in a joint to create a body entry which is small compared to that normally required in a cold knife procedure. By using a miniature rotary cutter that slides into the cannula, the surgeon is able to debride tissue fragments that are responsible for joint deterioration, disease and arthritis.

The present invention deals with a system in which a laser beam projected through an arthroscope functions as a non-mechanical surgical tool. The use of laser energy in medicine is now commonplace. Laser beams are used, for example, in skin treatment, in eye repair and in surgery. The main concern of the present invention is with surgical applications in which a high power laser beam functions to both cut and cauterize and must therefore be focused onto the surgical target.

Ordinary light is non-coherent and is made up of random and discontinuous wavelengths and phases of varying amplitude. The principle characteristic of a laser beam lies in its coherence, which means that corresponding points in its wavelength are in phase. In surgical applications, lasers in current use are the Nd:YAG, the $CO_2$ and the Argon laser. In practice, the laser may be pulsed or continuous.

Laser light is usually more intense, more monochromatic and more highly collimated than light from ordinary sources such as tungsten-filament lamps. The intensity of laser light can be extremely high. Thus power densities of over 1000 MW/cm$^2$ are obtainable to produce a beam capable of cutting through and vaporizing solid materials. Lasers fall into four basic categories: solid state-optically pumped; liquid dye; semi-conductor; and gas. Together, these four laser types cover the spectral region extending from ultraviolet to infrared.

The present invention will be described chiefly in the context of knee surgery, for meniscectomies and synovectomies are among the most frequently encountered surgical problems for which arthroscopic surgery is the appropriate solution. It will, however, be recognized that the surgical applications are by no means limited to these procedures, and that the invention is useful wherever the need exists to direct a focused $CO_2$ laser beam toward a surgical site in a path other than line-of-sight.

The invention is also useful in those industrial applications which require a steerable and focusable laser beam.

Though standard arthroscopic techniques employing miniature surgical cutting tools yield good results, they have been hampered by difficulties encountered in tool miniaturization and in site designation during the surgical procedure. Due to size constraints the accuracy with which miniature tools can be manipulated and placed has imposed practical limits on arthroscopic surgery.

A carbon dioxide laser has distinct advantages over other types as an effective surgical tool, for it cuts a visible and extremely clean line with very little backscatter, and it is capable of applying enormous amounts of energy onto a tissue site, thereby vaporizing the tissue into its gas constituents and leaving no biological residue. Because a $CO_2$ laser beam can vaporize any biological target such as cancer cells, it creates an absolutely sterile wound site devoid of biological contaminants. Moreover, the $CO_2$ laser lends itself to a precise level of control and can therefore be set to cut through one cell layer at a time in almost any cell substrate, or to burn through several millimeters of hard tissue, whichever procedure is indicated.

Despite its marked advantages over other types of lasers, the use of a $CO_2$ laser beam has hitherto been unavailable in arthroscopic surgery, for a $CO_2$ beam cannot be conducted through a fiber optic conduit. A $CO_2$ laser beam has a wavelength of 10.6 micrometers which lies in the infrared region of the spectrum and is therefore too long to be transmitted through existing fiber optic light conduits. As a consequence, the $CO_2$ laser in the field of surgery has heretofore been limited to those applications which do not make use of a fiber optic conduit for conducting the laser beam.

In arthroscopic surgery, the usual practice is to employ a cannula having a 3-5 millimeter diameter. If one seeks therefore to integrate a $CO_2$ laser with an arthroscope to perform surgery on a joint such as the knee, the requirements of the surgical procedure then dictate that the laser beam be orientable and be capable of travelling around corners. Beam steering expedients such as motorized lenses and rotating mirrors are not only expensive, but they are difficult to incorporate in a small bore arthroscopic cannula. As a consequence, use has not previously been made of a $CO_2$ laser in knee surgery.

In arthroscopic surgery, the object is to remove tissue particles from joints (meniscectomies and synovectomies—i.e., removing tendril-like particles of the meniscus and synovia). In other types of surgery such as in prosthetic hip, shoulder and knee implants, the aim of the procedure is to debride and polish particular areas of bone or tissue to create a socket whereby the prosthesis can then be driven into a precisely contoured socket.

In order to carry out orthopaedic surgery in soft or hard tissue with a laser beam, the operating surgeon must know just where cutting is taking place. The surgeon does not have a scalpel in his hand as a cutting tool; hence it is only by visual observation that he can sense his laser incisions, not by tactile sensation. Nd:YAG and Argon types of lasers make it difficult for surgeons to accurately evaluate the parameters of their incisions, for these have a short wavelength and exhibit backscatter characteristics. Backscatter or distal tissue penetration, is a phenomenon experienced when a laser beam having a short wavelength impinges on a visible target surface, the beam penetrating the target to a depth beyond that which can be visually observed. This penetration in depth heats and volatilizes the tissue in the backscatter region underlying the exposed target surface which is the only visible area of impact. This region assumes a non-linear geometric form that is a function of the type of cells and tissue which border one another in the region subject to backscatter effects.

An Argon laser is centered at about 0.512 micrometers in the wavelength spectrum, while that of an Nd:YAG laser is centered at about 0.532 micrometers. These shorter wavelengths are comparable to ultraviolet or blue-green light at the upper end of the light spectrum, as opposed to infrared radiation at the lower end. As a consequence, an Nd:YAG or an Argon laser beam will penetrate flesh, tissue and water, the beam transferring its energy to pigmented tissues beyond the surface of beam impingement. Because of the backscatter experienced with Nd:YAG and Argon laser beams, this gives rise to deleterious tissue destruction.

In contradistinction, a $CO_2$ laser generates a long wavelength beam having a 10.6 micrometer wavelength which lies in the infrared portion of the light spectrum. The energy of a $CO_2$ laser beam is fully absorbed by water and therefore by cells composed mostly of water. As a consequence, those cells in the target surface which are directly exposed to a focused $CO_2$ laser beam are the only ones destroyed, for there is virtually no backscatter. The energy transmitted to the focal point is almost entirely absorbed by the water in the local cells, and the energy penetrating the region beyond this point is at a very low and innocuous level.

As noted previously, in arthroscopic surgery, the usual practice is to use a cannula having a 3-5 millimeter diameter. If one attempts to integrate a $CO_2$ laser with an arthroscope to perform surgery in joints such as the knee, the requirements of the procedure dictate a steering action by which one is able to direct the laser beam around corners toward the site of interest. While a flexible fiber optic conduit is capable of directing light conducted therethrough in any desired direction, a conduit of this type is not useable with a long wavelength $CO_2$ laser beam. And though it is possible to steer a $CO_2$ laser beam with rotating mirrors and motorized lenses, these expensive expedients are difficult to incorporate in a small bore cannula.

3. Prior Art:

The patent to Swope discloses a photo-coagulation technique in which the beam from a gas laser is directed by an optical system created by a series of mirrors to the site to be treated. In the Kawaski U.S. Pat. No. 4,174,154, a condenser lens and a series of mirrors is used in conjunction with a $CO_2$ laser beam to direct the beam to a desired site. In the $CO_2$ laser beam endoscope shown in the Worster U.S. Pat. Nos. 4,211,229 and 4,141,362, a lens system is used to bring the beam to a focus. The Frank U.S. Pat. No. 4,313,431 makes use of fiber optics in an endoscope to conduct a laser beam.

The U.S. Pat. No. to Bredemeier 3,796,220 shows a stereo laser endoscope using a $CO_2$ laser which is focused by means of a lens and a reflecting mirror to provide a fixed focus system, the lens being so chosen as to focus the laser beam on a point lying in the focal plane of a microscope.

SUMMARY OF INVENTION

In view of the foregoing, the main object of this invention is to provide a surgical system which makes use of a carbon dioxide laser whose beam is conducted through a small bore cannula in an arrangement wherein the focused beam is steerable to impinge onto the site of interest.

More particularly, an object of this invention is to provide an arthroscopic system of the above type capable of generating a wide beam divergence angle close to the tissue in a deep cavity remote from the terminal lens whereby the action of the focused laser beam is concentrated at the surgical target and the tissue underlying the target is unaffected thereby.

Also an object of the invention is to provide in a carbon dioxide laser beam surgical system precise focal length control in real time as well as real time position control in the X, Y and Z axes.

Yet another object of the invention is to provide a surgeon with a fully integrated, accurate and easily controllable $CO_2$ laser system.

Briefly stated, these objects are attained in a laser beam surgical system provided with a cannula insertable into a body passage leading to a surgical site. The cannula includes a rotatable inner tube whose inlet section has two input ports, one being in line with the tube axis and being coupled to a white light source, the other being at right angles to the axis and being coupled to a carbon dioxide laser projecting a collimated beam. Supported at a 45° angle within the inlet section is a pellicle that is permeable to the beam of white light impinging thereon and reflective to the laser beam whereby both are directed toward an outlet section at the other end of the tube. Supported within the outlet section at a 45° angle with respect to the tube axis is a normally planar reflective membrane which directs both beams through a lateral output port toward the surgical site which is illuminated by the white light. The geometric center of the membrane is coupled at its rear to a controllable actuator which forces the membrane to assume a concave form acting optically to bring the laser beam to a focus at a target surface on the surgical site.

OUTLINE OF DRAWING

For a better understanding of the invention as well as other objects and further features thereof, reference is made to the following detailed description to be read in conjunction with the accompanying drawings, wherein:

FIG. 8 schematically illustrates the system as it operates in conjunction with television viewing.

DETAILED DESCRIPTION OF INVENTION

Operational Modes:

All lasers, regardless of type, function in one of two operational modes. The simplest, which is the axial or Fabry-Perot mode, operates in integral multiples of 2 pi phase changes. A second modal permutation is the TEM or Transverse Electromagnetic Mode. TEM modes are reproducible cyclic phase fronts which are self-propagating in any cavity in which they can reproduce in one complete round trip in that cavity.

Each of these modes is partitioned into several geometric orders. These are designated $TEM_{pq}$ ('p' and 'q' designate the orthagonal nodes). We shall concern ourselves only with lasers that operate in the $TEM_{pq}$ modes. TEM lasers generate many different wavefront geometries. In surgical procedures only two of these geometries are significant. One is the $TEM_{00}$ and the other is the $TEM_{10}*$ geometry.

A $TEM_{00}$ mode laser generates a typically Gaussian wavefront. Since its energy distribution is Gaussian, when impacting tissue sites, it creates a uniform cross-sectional heating front. Its output description can be likened to the Fabry-Perot oscillation because the phasing characteristics are virtually identical outside of the laser's oscillation cavity. The Gaussian energy front of the $TEM_{00}$ laser is useful because the focus of the laser contains 0.865 of the total power contained in the beam envelope.

The laser generates a light wave front with its energy peak at the axial dead center of the beam. Since the center of the beam is where the energy is concentrated, the periphery, measured radially from the dead center to the circumference, is at a slightly lower energy level as the edge of the focal point is approached. Because the beams are focused and the foci are small in size (3.0, 1.0, 0.1 millimeters and smaller), the energy density as a practical matter can be assumed to be uniform across the cross-section of the prime focus. Only when the laser power is reduced to a low level or the laser is modified to project a wide beam does the effect become noticeable.

The other mode used in some surgical procedures it the $TEM_{10}*$ mode. This is commonly called the donut mode in that the cross-sectional map of its energy distribution resembles a donut. It occurs because the nodes of the phasefront propagated in the laser cavity rotate with real time. Since the energy is concentrated at the circumferences of the focal spot, the beam will destroy the tissue at the edge of the prime focus, thereby leaving the tissue in the center of the ring intact. This type of wavefront can be useful because of the laser's controllable heat transfer as well as its backscatter characteristics.

The $TEM_{10}*$ phenomenon allows a surgeon to choose a target and destroy tissue on the periphery of a healthy central mass. Because of the differential phasefronts and the unusual geometry of the energy envelope, the $TEM_{10}*$ laser has a limited number of uses. This is not to downgrade its useability, but in most conventional surgeries the surgeon must have close control over a beam of predictably uniform power distribution. Therefore the use of $TEM_{10}*$ lasers is limited to highly specialized surgical situations.

Energy:

The basic unit of power used with all lasers is the joule. Power can be varied by modulating the laser beam's amplitude; hence surgical lasers include means to control the power input into the lasing system and therefore the intensity of the energy output.

Time or duration is the second power-related variable in a laser beam system. Duration is the length of time the energy remains over the subject tissue. It is inherently variable in all lasers in that the on-off control for the laser is via a foot switch used by the surgeon, or it is preprogrammed into a pulse train network which can be initiated or reinitiated at the surgeon's option.

The critical variable in a system according to the invention is that of beam area. This is directly related to spot size and therefore to focal length, cutting zone depth, and focal control. This variable is of primary concern, for it is dependent completely on the terminal optics of the laser's lens system. Such a lens system is attachable to any laser generator and therefore influences with the greatest degree of variability the amount of energy that can be transferred to the tissue.

As previously indicated, the $TEM_{00}$ mode laser operates with a Gaussian wavefront that concentrates 89.5% of the energy at the focus of the beam. This then makes it possible to change the total energy $E_t$ by altering the area A of the beamfront (spot size). By reducing the value of A by making the area smaller, the energy density is enhanced and therefore $E_t$ is caused to increase. Conversely, making the value of A larger diminishes the energy density and decreases $E_t$ accordingly.

The total energy value $E_t$ is critical in surgery because in certain circumstances one may not wish to vaporize tissue but only to coagulate it. Coagulation is a moderate heating of the tissues such that the collagen fibers depolymerize and repolymerize, thereby becoming sticky and inducing hemostatic coagulation. When cutting, the tissue is vaporized or blown apart by the high temperature and shock of the impact of the laser beam wavefront on the tissue. Since cutting requires more energy than coagulation, coagulation therefore calls for more control over the value of $E_t$.

Ultimate flexibility of control hinges on the control of the value of A, the area or spot size. It is the most difficult parameter to control because of the paradox of lens convergence angle versus focal length. The critical variable for the laser cutting or coagulation of tissue is the energy density applied to that tissue.

Beam Angle:

In arthroscopy and in other types of internal surgery where the surgical entry wound is a small hole rather than a large scalpel cut, the focal characteristics of the laser are critical, for these determine the dimensions of the cutting zone. As noted previously, both Argon and Nd:YAG lasers have high levels of backscatter, creating deep zones of distal tissue destruction that cannot be seen from the surface.

With the $CO_2$ laser, this is not the case, for the area of impact is the only area of tissue destroyed. Since a $CO_2$ laser can have a very hot focus and as it is equipped with a long focal length narrow beam divergence angle lens, it can cut through a great depth of tissue in a very short time.

In areas where the tissue is very thin or where the tissue fragment to be excised, as in a meniscectomy, is immediately in front of healthy tissue, great care must be exercised in controlling the depth of cut. This constraint, from a surgical and anatomical point of view, which requires the destruction only of targetted tissue and not tissue distal to the point of impact, makes the beam divergence angle of the $CO_2$ laser a critical factor.

To better appreciate this problem, let us consider an elementary lens. A typical thin convex lens has a specified focal length ($f_o$=prime focus). This is the point in space where the rays of light transmitted through the lens converge and represents the point of maximum light intensity. This means that all of the parallel rays which enter the lens from one side emerge from it, forming a sterian (solid angle $\theta$) to converge at one point. Any point displaced from the focus along the axis of the lens has a lower energy density due to the larger zone of dispersion of the light rays.

The focal point is finite, hence, the rays of light which travel in straight lines away from the lens at specified angles from the lens' surface not only converge at the focal point but diverge beyond it. The beam widens and therefore diverges past the focal point at the same angle at which it converges to the focal point (angle $\theta'$). The angle of convergence is then equal to the angle of divergence ($\theta = \theta'$). This phenomenon, which makes it possible for the surgeon to cut with the laser, also hampers his ability to use the laser at long distances from the target.

If one uses a laser with a long focal length optical system (a long distance between the lens and the focal point), the beam's "cutting zone" is large and therefore deep. If one uses a laser with a short focal length optical system (short distance between the lens and the focal point), the cutting zone is small.

When the angle of convergence is large, the angle of divergence is likewise large and the laser's energy is only concentrated close to the focal point. Any point displaced from the focal point, either side on or off axis, is at a much lower power density. Thus, short focal length lenses have a large angle of convergence and a concomitantly large angle of divergence and therefore have a very narrow cutting zone. When the angle of convergence is small, the resultant angle of divergence is also small. And because these angles are small, they concentrate the heat energy of the laser in a small area for a longer linear distance.

Thus long focal length lenses (100 millimeters or more) have very narrow angles of convergence and therefore very narrow angles of divergence, creating a long distance about the focus on axis where the beam is sufficiently concentrated to perform cutting operations. When a particular case requires a very narrow cutting angle, the surgeon also has the greatest depth of cut. This comes automatically because of the necessity for a long focal length lens. When a lens with a wide beam divergence angle is used, the terminal lens has to get very close to the surgical target. This rule imposes a restriction on the surgeon which in many cases is contrary to the requirements for accomplishing necessary surgical tasks.

The distance from the terminal lens (objective) to the prime focus is critical because of the relationship between focal length and working distance of the laser. Infrared-transparent lenses which are currently available are made of zinc selenide, gallium arsenide, zinc sulfide and other metals. These have a short focal length (wide divergence angles, hence close operating range) and must be large in diameter in order to achieve acceptable quantum efficiency. Their large physical diameter coupled with their wide beam divergence angle critically limits their use at any distance from the surgical target and precludes their use in a cannula.

However, one of the advantages of using a lens with wide beam divergence is that once the prime focal point is set and the target lased, the beam disperses so fast that in a very short distance (0.5 to 2.0 millimeters away) the energy density is low enough that the beam will not cut or critically heat distal tissue. This is an advantage where surgical procedures are required to remove one or two cells or a single layer of cells at a shallow depth.

The cannula, which must be from 20–40 centimeters long in order to reach into a cavity, would require that the lens be mounted at its terminus. This construction would require extremely complex sub-miniature linkages to control the prime focus of the lens. In addition, the lens would be subject to clouding, abrasion, direct tissue contact and contamination. The lens' primary constituents, zinc and selenium, are toxic metals. Beam position control would be difficult too because positioning would only be possible by moving the entire cannula assembly. This technique lends itself neither to precision control or to speed. It would seem therefore that the surgical requirements for laser arthroscopy and the cutting characteristics of the laser and its optical control system are working at cross purposes.

Anatomical Factors:

In knee surgery, two things are required from a laser. First, the surgeon must be able to deliver the laser beam onto the target, and second, the laser beam must cut the target and nothing more. Knee tissue, like most body tissue, is convoluted and three-dimensionally contoured. Unwanted damage of peripheral tissue can cause complications and anatomical difficulties. In order to avoid this problem the surgeon must have a carefully focused laser beam, a clear target and the means to deliver the beam accurately to the target.

Focus of the laser beam without regard to divergence and convergence angle (length of the cutting zone) can cause serious problems. Since the focal point does not account for or indicate convergence or divergence angle (only cross-sectional area on the target), it is possible that a non-optimal (wrong focal length) lens might be used.

A 1.0 cm diameter, 400 millimeter ($f_o$) lens will focus a laser beam at an included angle of 1°30′, providing cutting energy density levels for 5 centimeters on both sides of the prime focus with a 2.0 mm spot. This means that when the beam is focused on a target and the laser is fired, the first pulse of the laser beam vaporizes the target and the second pulse can travel through the now vaporized target's space and, because of its small divergence angle, impact tissue distal to the target, destroying that tissue.

The requirement for a long focal length lens is based on the need to get the beam through a long arthroscope onto a deep or remote target. The inability of the $CO_2$ laser to be used with fiber optic light guides has rendered it impossible to use in arthroscopic surgical situations because of the length of the arthroscopes, most of which are in the order of 20–40 centimeters in length. This is too long to incorporate lenses of useful focal lengths and acceptable quantum efficiencies in their bodies.

If one attaches a beam splitter and viewing head to an arthroscope having a 20 centimeter length and assumes that the target will be one centimeter from the arthroscope's terminus, one then has a 35–40 centimeter distance between the laser's parallel light output and the arthroscope's cutting aperture. This distance demands a lens which has a focal length of 300 to 400 millimeters. Given a lens with a beam convergence and divergence angle of 2.0 to 0.5 degrees yields a cutting zone depth from 10–25 centimeters ($\pm 12.5$ centimeters on either side of the prime focus).

Under these circumstances, once the meniscus fragments are blown away, there remains the possibility of the laser beam cutting 5 to 12 centimeters deeper into the tissue and perhaps out the other side of the knee or sufficiently far to damage healthy tissue distal to the target. This limitation is the problem which blocks the use of the $CO_2$ laser in standard arthroscopic hardware with conventional lens systems. Since the surgical anatomy of knees and other joints is irregular and multi-geometric, the ability to control the focal point and the depth of the cutting zone of the laser is of critical importance.

A large convergence angle (short focal length) lens demands that the terminal lens be very close to the target area. Since the laser cannula can only be 3-5 millimeters in diameter, this size constraint puts an extreme burden on the lens designer and restricts the quantum efficiency of the lenses. He does not have 300 to 700 millimeters of focal distance with which to design a lens which can be held outside of the body and therefore is large enough to efficiently focus the laser light on a distant target. The technical difficulties surrounding the making of a small diameter, high angle of convergence quantumly-efficient lens are therefore considerable.

A laser beam system having a long focal length and therefore a shallow convergence angle is a definite hazard, but it fulfills the optical path length requirements for the arthroscope. A short focal length, high convergence angle beam is a definite advantage, but cannot be used at the end of a 40 centimeter optical path. The difficulties created by this situation are such as to call for some solution other than that of a conventional lens formulation. The solution provided by the present invention is a system having the characteristics of small diameter optics as well as the ability to generate a high convergence angle light beam in a small diameter with a variable focal point. It has to allow for adjustment in the depth of cut at the same time the focal point area is adjusted to preserve the ability of the surgeon to control tissue destruction caused by the laser beam at the specific focal point.

In addition to the mechanical requirement of this type of surgical procedure, secondary surgical effects (consequential tissue trauma) must be minimized. Such trauma is caused in part by the movement of the arthroscope and of the associated implements through large angles and the subsequent stretching and tearing of tissue immediately in contact with them. An instrument in accordance with the invention is designed so that relatively little physical displacement is necessary once the single cannula is inserted into the joint. This, in turn, minimizes tissue trauma while providing the surgeon with all of the required beam maneuverability.

In a laser cutting system, the angles indicative of the degrees of displacement that the instruments must transverse for the surgeon to reach the appropriate areas of the tissue to be lased are rather large. The insertion points are not necessarily at the vertices of the angles and the trauma caused to the skin, musculature, and vascular micro-structure is substantial. To add to the problem, when standard arthroscopic instruments are used, additional punctures must be made for effluent irrigation, affluent irrigation, and for the mechanical cutting system (arthroscopic cutter or scissors) to do the actual tissue removal. This can require as many as three large punctures.

A laser steering cannula in accordance with the invention virtually eliminates all of the angular displacement by using rotational angular changes to reach the surgical target. Hence, with the present system there is only one large puncture, a minimum of tissue trauma, and disturbance to the vascular micro-structure.

Inflation Media Requirements:

In standard arthroscopic surgical procedures, liquid is used to inflate the knee or whatever joint is involved, for the joint parts need to be separated. In the case of the knee, one must separate the tibia from the femur and the paletta so that the synovia and meniscus can be viewed and operated on.

To be effective in this context, the inflation medium must be biologically inert, and it must not give rise to any distentum or turgor of the tissues or any emboli. Nor should the medium readily diffuse into peripheral tissue or blood. The inflation medium should be easy to apply to the patient and be free of unwanted side effects such as drying of the tissue, for this may result in peripheral vascular or cell damage. Finally, the medium should lend itself to easy control by the surgeon and be economical to use.

During the typical arthroscopic procedure, normal physiological saline is injected under pressure into the knee through a needle. Physiological saline is used because it is the standard inexpensive, biologically-neutral and absorbable material which is available. In addition, by circulating a flow of saline, debris and particles of resected tissue can be removed with little difficulty.

Surgeons, by means of television cameras, are now able to look into the knee through arthroscopes and to view what is going on when the liquid circulates around the surgical site. The surgeon can observe on a video screen the debridement characteristics of the liquid upon the surgical premises. Since lasers have not heretofore been useable in arthroscopes for the reasons previously explained, the inflation medium has never been of consequence.

With the present invention which makes it possible to use the $CO_2$ laser through an arthroscope, physiological saline can no longer be used as an inflation medium. The reason is that physiological saline is water with 0.8% salt content, and the 10.6 micrometer wavelength of $CO_2$ laser light is fully absorbed by the water. Thus, if physiological saline was used as the inflation medium in an arthroscopic laser surgical procedure, all of the $CO_2$ laser's energy would be converted to heat by the water. As a consequence, the water will possibly boil, thereby generating tissue burning steam. It is therefore evident that a water-based liquid medium for inflating the knee is interdicted in a $CO_2$ laser arthroscopic procedure. Thus the logical choice for the inflation medium is a gas.

The two gases that have been regularly used in surgical procedures are diatomic nitrogen and carbon dioxide. These gases have properties that make them useful in surgical procedures, for they are fairly stable at normal operating temperatures and pressures, they are readily available and economical, and they have minimum toxicity to exposed tissue. Moreover, these gases displace water readily, have fairly high boiling points, and do not freeze at lowered body temperatures. However, these gases exhibit serious disadvantages when used in conjunction with $CO_2$ lasers which rule out their use as an inflation medium.

Diatomic nitrogen is stable at low temperatures but at elevated temperatures it tends to combine with hydrogen and oxygen to form nitric acid and nitrogen compounds which include nitrous oxide, nitric oxide, etc., all of which are injurious to protoplasm. Nitric acid resulting from the reaction of nitrogen gas with hydrogen and oxygen at high temperatures is destructive to all tissue, especially nerve tissue (which is most susceptible because of its protein makeup).

In a normal surgical procedure, the use of a $CO_2$ laser to vaporize or destroy tissue creates an impact site temperature well in excess of 1000° Celsius. This temperature is high enough to destablize almost any nitrogen-bearing compound. These include hydrocyanidic acid, cyanide, nitric acid, nitrogen dioxide, and nitrous oxide. None of these compounds are desirable in vivo or at an operative site. To further add to the medical risk is the possibility that these compounds might become trapped inside a body cavity. The potential of biological damage and post-operative complication is high with nitrogen gas chemistry should it be used as the inflation medium with a $CO_2$ laser. Nitrogen gas is therefore not an acceptable inflation medium for use with the $CO_2$ laser.

Carbon dioxide, which is also in common use in surgical procedures, does not possess quite so many of the undesirable characteristics of nitrogen at elevated temperatures. However, at the laser's impact site, carbon dioxide will disassociate into its constituent molecules. These, in the presence of the protein and amine-based compounds of which our bodies are made, can generate hydrocyanic acid and cyanide gas.

Carbon dioxide has another characteristic which makes it even less acceptable for use with the $CO_2$ laser. This characteristic is the ability of carbon dioxide to trap heat, for it is an excellent thermal insulator. The 10.6 micrometer (far infrared) wavelength generated by the laser is almost completely contained by carbon dioxide gas. This phenomenon will impede the surgeon's ability to keep the wound site cool and hence the ability to protect peripheral tissue damage from thermal exposure.

The requirements for an inflation medium in arthroscopic surgery clearly point to the choice of a gas that is thermally stable, chemically inert, and of low solubility so that it will not dissolve into tissues rapidly. We have found that helium and argon satisfy these requirements. They are both inert monoatomic gases, they share equivalence sports in the periodic chart, they do not react electrically and both gases are good conductors of heat.

Though helium has a high osmotic permeability coefficient because its atom is even smaller than a molecule of hydrogen, it does not readily dissolve into tissue at low pressures. Argon, on the other hand, is a substantially larger atom. It does not have the permeability coefficient of helium, but it does have a tendency to dissolve into fluids and tissues of the body. However, neither of these gases will give rise to chemical and electrochemical effects when excited by high temperatures.

From strictly thermal considerations, either helium or argon could be the medium of choice for inflation for arthroscopic laser procedures. Both He and Ar have the ability to absorb the heat generated by the $CO_2$ laser and will facilitate cooling and thereby limit the transfer of heat to peripheral tissue in the surgical area.

When considering argon and helium gases as media, it must be noted that the specific heat of helium is 1.24 and that of argon is 0.124. This difference indicates that helium absorbs much more heat than does argon; therefore, the ability of helium to cool the laser target area and maintain the peripheral tissue temperature is an order of magnitude greater than that of argon. In addition, the entropy $S°$ of helium is less than argon. The value for helium is 30.13, while argon is 36.983. These differences are substantial and the practical application of the entropic differentials and of energy transfer per unit per degree Kelvin are not insignificant in the context of the present invention.

Helium is much more soluble in blood and therefore does not present the problem of the blood retaining quantities of it and becoming saturated under elevated pressures because it gasses out as fast as it dissolved. It does not generate the potential of forming micro-emboli at surgical working pressures.

Since the body is an isothermic system with built-in regulators, we can assume that temperature functions and the effect of the heat absorbed by the inflation gas when it expands, in relation to the total thermal mass of the body, is negligible. This means that the influence of the body heat on the solubility of the gases of the blood in terms of a differential driven process can be ignored. Helium is much less soluble in blood than is argon.

It is clear therefore that for use in conjunction with $CO_2$ laser surgery, helium gas is the preferred inflation medium. Because of its high specific heat, helium has the ability to absorb and transfer heat away from the laser impact target to the atmosphere. Helium is inert at all temperatures, it is easy to handle, and can safely be used in the operating room from the standpoint of both chemical reactivity and ionization hazards.

Helium Delivery System:

Delivery methods for helium are not complex, but there are several considerations that must be taken into account. One of these stems from a phenomenon associated with the laser beam's impact on tissue, called "beam masking". The material at the impact site is literally blown apart into its constituent elements. Should the target be a solid material such as bone (calcium phosphate), the surface of the bone will be vaporized and thereby broken down into elemental compounds, and the sub-surface layers will be fractured and fragmented by the shock wave caused by the laser's impact.

Particles will dislodge and be scattered in a means similar to the impact of a high explosive projectile on the ground. These particles and dense gases create a smokescreen which can totally block the laser beam. When this occurs, the procedure must be stopped. If the target continues to be lased, the gas and obstructing media continue to heat up, adding heat to the wound site and raising the mean temperature of the peripheral tissue to an unacceptable level.

In order to ensure that the $CO_2$ laser's beam path stays clear (minimum beam masking), the inflation medium should be conducted through the cannula of the laser arthroscope device. This will provide a constant stream of gas pumped through the laser tube to keep the laser clear of scattered debris, dense gas, blood products, and materials which might otherwise lodge in the tube or cloud the beam path, impairing the laser focusing device and the delivery of the laser beam.

Figures 1, 2:
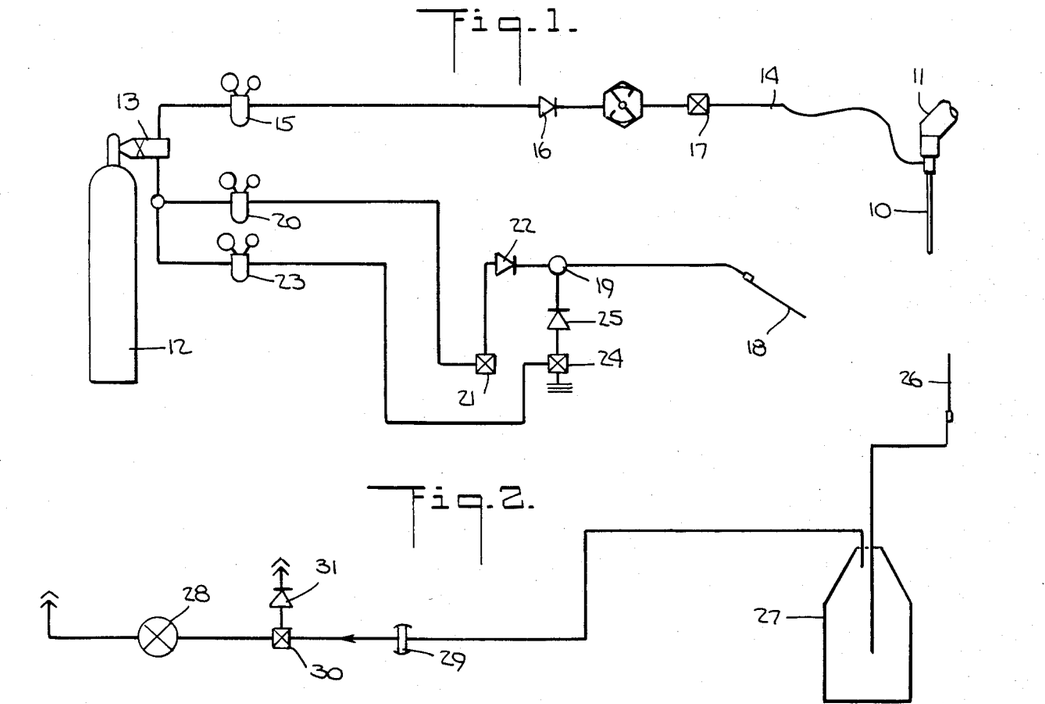
FIG. 1 is a block diagram of a helium gas system in accordance with the invention for inflating the surgical site.
FIG. 2 is a block diagram of a gas evacuation system in accordance with the invention to be associated with the inflating system.

FIG. 1 schematically shows a laser arthroscope 10 in accordance with the invention operating in conjunction with a $CO_2$ laser 11. Supplied to arthroscope 10 is an inflation medium derived from a helium supply cylinder 12. The helium from the cylinder is fed to the cannula of the arthroscope through a helium manifold 13 and a line 14 extending from the manifold through a regulator 15, an anti-backflow valve 16, and a start/stop switch 17 which interlocks with the laser.

The gas delivery and circulation system is preferable controlled by regulating the output or the low pressure side. This serves to keep a steady circulation of uncontaminated gas through the wound site so that materials resulting from the high temperature decomposition of organic products do not build up; hence heat generated by the laser is removed.

To this end, a purging tube 18 is provided which is coupled to manifold 13 through alternate paths at a junction 19, one being through a low-pressure regulator 20, a switch 21, and an anti-backflow valve 22, the other being through a high-pressure regulator 23, a foot-operated on/off switch 24, and an anti-backflow valve 25.

The system shown in FIG. 2 makes it possible to remove the gas easily from the surgical site and opposite of the area of surgical interest. As has been stated, it is necessary to keep a constant flow of helium at a constant pressure through the laser cannula and across the surgical target. This allows both tissue cooling and provides an inert target envelope which further reduces the probability of poisonous compounds being formed as byproducts of the high temperature vaporization beam.

To effect gas removal, evacuation cannula 26 is placed immediately behind (or to the side of) the surgical site so as to create a "draft" across the surgical target. This technique ensures proper flow of gas around the surgical site which will facilitate proper cooling and keep the area swept clean of interfering clouds. The draft effect of the gas helps to suck away and debride surgical rubble and particles from the wound site, allowing the surgeon a continuously clear view of the target.

In the arrangement shown in FIG. 2, evacuation cannula 26 is coupled to a collection container and smoke filter 27 which is coupled to a vacumn pump 28 through a vacumn safety valve 29 and a source select switch 30 which is linked to the atmosphere through an anti-backflow valve 31.

Vacumn pump 28 provides negative pressure at the output rather than simply venting the helium to the atmosphere. If the gas is simply vented to the atmosphere, control over the inflation (distention level) of the knee is limited, for one is not then able to control back pressure. Effluent pumping makes it possible to accurately balance the helium input against the output and to accommodate another helium jet directed toward specific contaminants or to provide additional cooling of sensitive tissue.

Figures 3, 4:
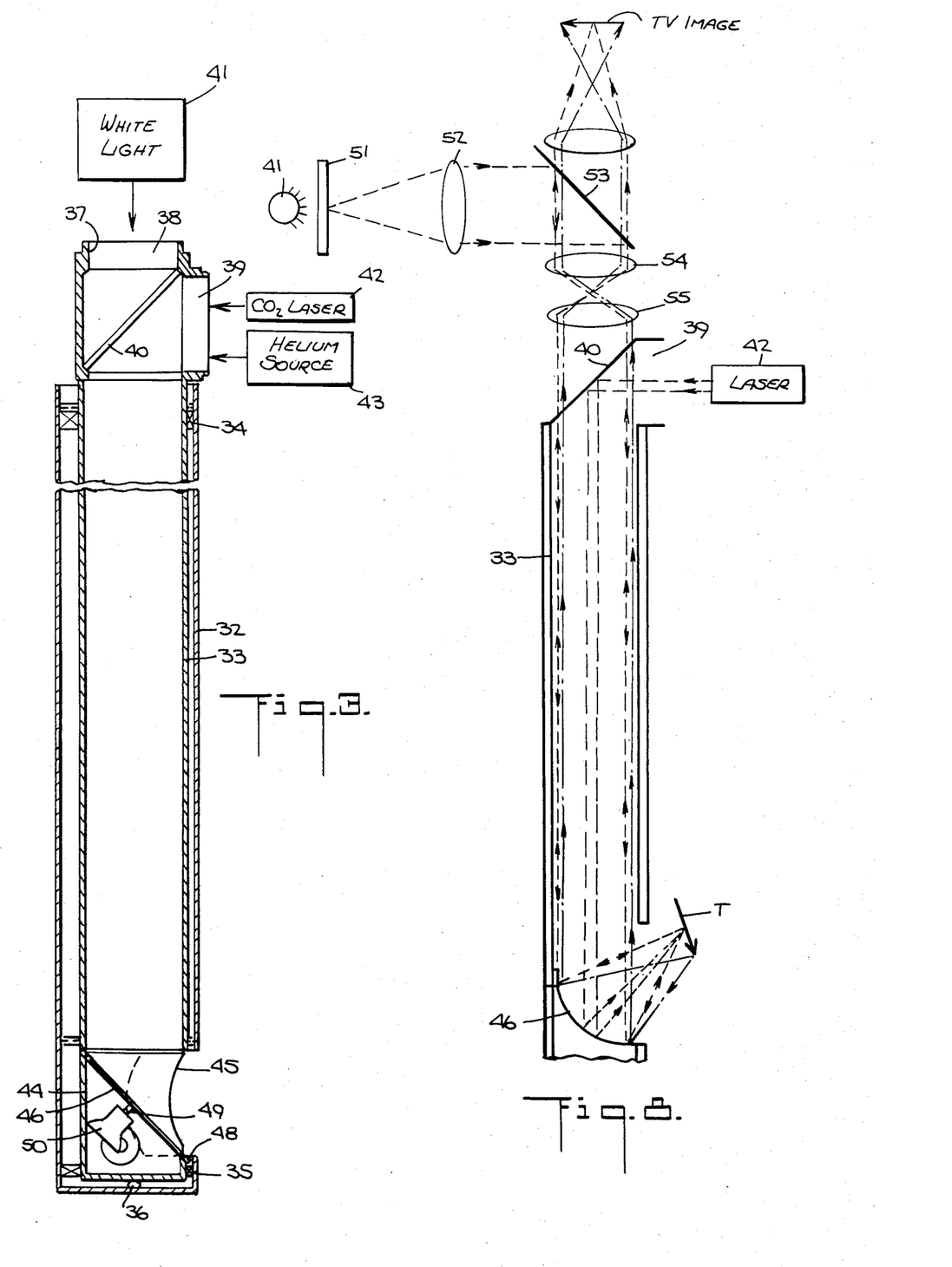
FIG. 3 is a sectional view of a system including a laser beam cannula in accordance with the invention.
FIG. 4 illustrates the membrane mirror included in the cannula.

The Laser Beam System:

Shown in FIG. 3 is a laser beam system in accordance with the invention for performing a surgical procedure in which a laser beam is focused on a target at a surgical site. The system includes an elongated cannula constituted by an outer tube 32 and an inner tube 33 coaxially supported for rotation within the outer tube by upper and lower annular bearings 34 and 35. Thus one can turn the inner tube relative to the fixed outer tube to direct the beam as required. The lower end of the inner tube is closed by a flat plate, as is the lower end of the outer tube, a thrust bearing 36 being interposed between the end plates. The cannula is insertable into a body passage leading to the surgical site.

Attached to the upper end of the inner tube 33 and projecting beyond the outer tube 32 is an inlet section 37. Inlet section 37 is provided with a first input port 38 which is colinear with the longitudinal axis of the inner tube 33, and a second or lateral input port 39 at right angles thereto. Supported within the inlet section 37 is a semi-transparent mirror or pellicle 40 which is at a 45° angle with respect to input ports 38 and 39. The pellicle is optically permeable to white light and reflective with respect to infrared energy.

Coupled to input port 38 is a white light source 41 whose rays are collimated to produce an illumination beam which passes through pellicle 40 which is transparent thereto. The light beam is directed down the inner cannula tube 33 and serves to illuminate the surgical site for direct visualization or for television viewing as will be later explained.

Coupled to the lateral input port 39 is a carbon dioxide laser 42 whose 10.6 micrometer beam which lies in the infrared region, is reflected by pellicle 40 and directed thereby down inner tube 33 concurrently with the white light. Also introduced into lateral input port 39 is an inflation gas derived from a controlled helium source generally represented by block 43, the helium flowing through the inner tube 30 into the surgical site.

The lower end of the inner cannula tube 33 terminates in an outlet section 44 which is disposed within the lower end of the outer tube 32. Outlet section 44 is provided with a lateral output port 45 at right angles to the longitudinal axes of inner tube 33. Mounted within outlet section 44 at a 45° angle with respect to this axis is a deformable membrane 46 which is normally planar and is peripherally supported by an elastometric coupling 47 within an annular mounting ring 48. Thus the deformation of the membrane is not distorted at its periphery. The angular position of the membrane with respect to the axis of inner tube 33 creates a right triangular conic section which when viewed at a position normal to the plane thereof results in an ellipse, as shown separately in FIG. 4.

Attached to the geometric center of the elliptical membrane on the rear side thereof between the two foci and coplanar with its surface is a rigid drive pin 49. The pin is thermo-compression welded or otherwise fixedly secured to membrane 46. This pin allows forces to be exerted on the deformable membrane by an actuator 50 adapted to deflect it geometrically. These deflecting forces give rise to stress vectors and so alter the curvature and contour of the membrane as to define a concave aspheric mirror having optical properties making it possible to focus the laser beam impinging thereon.

The membrane may be made of an aluminized polyester sheet such as mylar, or of polished titanium, and acts to reflect close to 100% of the 10.6 micrometer wavelength light generated by the $CO_2$ laser. The light is focused by the concave membrane mirror at a point whose distance from the mirror's surface is inversely proportional to the displacement of the membrane. Thus when the membrane is planar, the laser beam projected through the cannula strikes the membrane and is reflected in a parallel beam. Since the light source is a laser, all incident rays are exactly parallel and coherent; therefore all reflected rays will be parallel. This parallel beam has the same area as that of the beam in the cannula and does not concentrate the light to a sufficiently high energy density to cut tissue.

The actuator 50 may be an electromagnetic or other electrically-operated mechanism capable of displacing the pin. When the pin is extended axially by activator 50 and thereby pushed toward deformable membrane 46, its contour is rendered convex. This shape disperses the light as a second order function of the distance of displacement and completely diffuses the beam to cause it to cover a very large area, thereby reducing its energy density and inhibiting the laser's ability to even so much as heat tissue. Conversely, when the pin is pulled down by actuator 50 so that it shapes the reflective membrane into a concave form, it then focuses the laser beam to a point. Since the membrane is designed to only assume the form of a quasi-parabolic section, the resultant focus is a single point.

This parabolic shape takes parallel rays and converges them to a point or the focus of the parabola. The focal distance from the apex (or the bottom of the parabola's trough) is a function of the parabola. By changing the quasi-parabola's contour, one can change the point at which the light is brought to a focus. This makes it possible to change the focal point of the laser beam by changing the shape of the parabola.

In order to obtain proper deformation of the membrane to form a quasi-parabola, we must arrange for proper deflection of the membrane mirror material. Since the quasi-parabolic shape is non-linear, it follows that the stresses that deflect the membrane must also be non-linear. But stress in a uniform material is a linear quantity having magnitude and direction. This raises the question as to how one can generate a non-linear stress to form the desired non-linear shape. Since we cannot alter the stress vector, we must control the cross-section of the stressed material so as to reproduce the function that we require.

Ordinarily when one uses an annularly-shaped membrane of uniform thickness and stresses it at its center, the resultant profile shape is a second or third order parabola. This is due to the build-up of stresses in the material. This shape is not acceptable, since that function gives us a close focal point, not a single focal point. This would, in effect, focus the beam into the mirror, making it useless for surgery.

Figures 4, 5, 7:
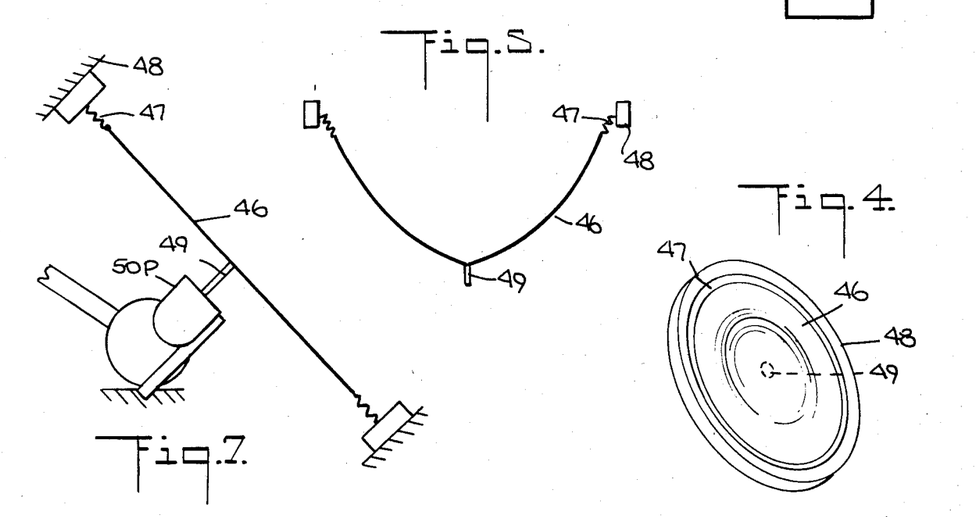
FIG. 5 schematically shows the shape of the membrane mirror when it is actuated.
FIG. 7 illustrates the relationship of the mirror and its actuator.

In order to circumvent the problem of parabolic deflection it is necessary to create a condition in the material which will force the stresses to build up in directions and at magnitudes which create a quasi-parabolic curve when the pin is pulled, as shown schematically in FIG. 5. Because the membrane 46 is located in its geometric center in a direction at right angles to its suspension plane and with a high displacement load, this places the focus on both the optical and geometric axis and in the aperture.

Figure 6:
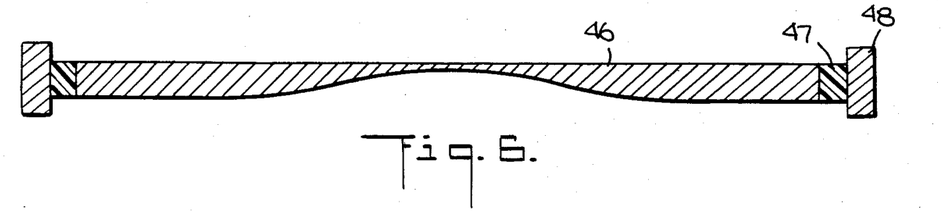
FIG. 6 is a section taken through the mirror.

The best way to accomplish this end is to contour the thickness of the membrane as shown in FIG. 6 so that the stress concentrations build up properly as they proceed radially from the center to the circumference. This will accommodate the decreasing material strength and distribute the stresses in a non-linear fashion across the surface of the mirror. Thus the membrane is thinnest at its center and becomes increasingly thick as one moves away from the center.

The tailoring and control of the cross-sectional profile of the mirror makes it possible to create non-uniform stresses in a material of uniform elastic modulus. Because of this we can use the non-linear deflection of the reflective membrane to create both on axis focal points and off axis focal points. Thus steering can be accomplished in off axis, off aperture focal points.

Since the membrane mirror shape generated by the laser focusing and steering device is aspheric, it has the characteristics of both parabolic and hyperbolic mirrors. The system is therefore unique because of its ability to generate both exceedingly sharp focal points as well as a short length of focal loci. The short length focal loci or line of focus can be controlled accurately in both depth and width. This makes it possible for the laser to bore a very neat cylindrical hole, thereby developing a uniform zone of tissue destruction and a minimum of peripheral tissue damage.

Because the membrane mirror operates on the principle of elastic deformation, it affords a large measure of engineering freedom as to the materials one can choose to implement its structure. Thin polished titanium is a preferred membrane material because of its high yield strength and its exceptional hardness which can be brought to a high optical finish. For some specific applications, an elastomeric polymer such as silicone rubber or neoprene rubber may be better suited. These can be molded cheaply into almost any cross-section and then treated with vapor-deposited aluminum for high reflectance.

The angular deflection of the deformable membrane and therefore the depth of the quasi-parabola and its conical aspheric shape, control the focal point of the laser beam. Because the inner tube of the cannula is mounted co-axially within the outer tube thereof, we not only can change the focal length, but we can also steer it by biasing the stresses on the pin off the axial centerline of the membrane.

To this end one may use an actuator 50 for drive pin 49 in the form of a piezoelectric actuator 50P as shown in FIG. 7 which can be electrically excited to displace the pin in either the X or Y direction whereby the beam reflected by the membrane can be displaced both in the X and Y axes. In addition, the inner tube 33 can be rotated within the outer tube 32 about the axis of the cannula to allow coverage of a fairly large arc sector. This makes it possible to control the beam in a three axis coordinate system with a high degree of precision. In practice, the piezoelectric actuator may be controlled by signal commands originating in a remote computer.

Because the helium-inflation medium is fed to the surgical site through the inner tube of the cannula, the gas is thereby channelled to concentrate at the laser's target site. This provides the ability to use the minimum amount of purging gas and to achieve the optimum effect.

Visualization:

As shown in FIG. 8, to facilitate television viewing light source 41 is arranged to direct its rays through a diffuser plate 51 and a lens 52 onto a beam splitter mirror 53 which is at 45° relative to the axis of the inner tube 33 of the cannula. Mirror 53 acts to reflect the light beam into the cannula through lenses 54 and 55 to be directed at the outlet section by the focusing membrane 46 onto the surgical target T which is illuminated thereby. The illuminated image of the target which passes through beam splitter mirror 53 is viewed by a TV camera through a TV lens.

The pellicle 40 which is reflective to the infrared light from laser 42 but transparent to white light, acts to send both the white light and the laser cutting beam down the cannula. Since both the white light and laser beams are focused by the same membrane mirror 46 (terminal device), the area or target point T that is in focus optically for visual siting and inspection is the same area or target point that is in focus for the laser-cutting beam.

This arrangement does away with the need for a second cannula opening close to the surgical site to make direct visualization or video observation possible, for the entire system is integrated with TV and direct visualization optics.

A highly significant advantage of this arrangement is that all of the beams—the visualization beam (light returning from the target to the eye of the observer or television camera), the illumination beam (the light that is transmitted through the beam splitter 53 which floods the target area with illumination), the coherent laser cutting beam (the $CO_2$ surgical cutting beam), as well as a HeNe pilot beam—all converge at the same point which is the focus generated by the deformation of the membrane mirror 46. As a consequence, the surgeon, visualizing the surgical target through the focusing system, is able to perceive exactly what is the target of the laser, this being seen in the dead center of the visible image and in precise focus. There is no focal differential between the white light and the infrared laser beams.

Conventional lenses that are transparent to a 10.6 micrometer infrared $CO_2$ cutting beam are opaque to visible light, whereas lenses that are transparent to visible light will absorb the 10.6 micrometer cutting beam. The absence of either type of lens in the cannula passage makes it possible for all of the beams to be bundled and allows them to fulfill their respective functions together. This is only possible by using a membrane mirror in accordance with the invention, for this mirror, unlike a lens, treats all light wavelengths in the same manner. The membrane mirror deflects light through reflection, not refraction, and the angles of reflection are not related either to the refractive index or to the dielectric constant of the material from which the mirror is made. There is no focal point shift as the wavelength of the light reflected by the mirror changes.

This characteristic which causes all beams passing through the cannula to focus at the same point, permits multiple wavelength broadband light to be coaxially superimposed on the laser, and permits visualization return and illumination beams. Thus Nd:YAG and Argon beams may be combined with a $CO_2$ beam to facilitate broader surgical utility of the laser system.

When the unit is assembled, it must be bore sited so that the helium-neon pilot beam, the $CO_2$ laser cutting beam, the white light illumination beam, and the visualization return beam are all exactly coaxial. All of these beams can then be treated as one bundle of light that is exactly parallel from its origin to its terminus (focus).

When using a television camera as the mapping device for a computer-controlled system, the television's raster scan generates the X and Y coordinates of the tissue in relation to the beam (and vice versa). Because of the coherent laser and white light reflection characteristics of the mirror, the focal point will be the depth. The amount of control used to deflect the membrane mirror can then be translated into a value which can be translated into a Z coordinate, thus giving the computer a three-dimensional, triaxial representation of the surgical field.

Though the illumination light is focused by the deformable membrane mirror, it is different from the laser beam because it is inherently diffuse. Since it is not coherent, it will diffuse over an area larger than the target area (surgical field). Thus the target area will be generally illuminated while the laser beam is focused at its dead center.

The steering membrane mirror affords ultimate control over the laser's focal characteristics by making practical the use of a wide beam angle source at long distances from the laser generator. The pragmatic benefit of this device is that a short focal length lens is put in close proximity to the tissue area of surgical interest. And though it mechanically acts like a long focal length lens, it has none of its disadvantages.

Because of the non-linear mirror and focal characteristics of this laser steering device, it is readily adaptable to the emerging technology of EXCIMER laser ablative surgery. Its optical characteristics make it possible to focus an EXCIMER laser without the need for a molybdenum mask to confine the beam. The elimination of the mask gives the surgeon more latitude in shaping and controlling the ablation while reducing the cost.

Computer Control:

The key to extending the use of this system is that the membrane mirror is the control point of a powerful laser beam energy source which may now be precisely directed. It therefore becomes feasible with the use of computer control to carry out procedures which have heretofore been too delicate, risky or tedious to attempt manually.

Because of the tremor of the human hand, the surgeon cannot hold a scalpel on a line with an excursion of less than ± half a millimeter. A laser beam's focal point can be smaller than 0.01 millimeter. Computer control allows maneuver of the membrane mirror within several ten thousandths of an inch, making precision control feasible. Indeed, control can be so accurate that the laser may be used to remove single cells or a layer of cells less than a tenth of a micrometer thick.

Among the uses of a system with this degree of accuracy and resolution are ultrafine vessel anastomosis, microscopic neurolysis and tenodesis, microscopic duct and vascular work, microscopic excision of carcinomas, microscopic neurosurgery, as well as other neurological repair applications. These procedures can be carried out by using various types of cannulated delivery systems similar to the arthroscope and laparoscope. With the computer controlling the direction, power density, focal length, spot size and pulse rate of the laser, the imprecision inevitably attending human control can be virtually eliminated.

A further extension of this technology is to couple the computer-manipulated laser with a television video camera scanning the target site. By using the computer to recognize and interpret the video algorithm (picture), this would allow manipulation of the laser cutting instrument at high speed through and around a set of bounded coordina. Those coordina could be defined by the presence of certain chemical dyes of selected color, pre-programmed cell topology, or programmed coordinate positioning.

Thus, cancer cells can be stained for identification and the computer's video interface then used to rapidly and accurately destroy, on a selective basis, only those cells that are identified. This would allow cancerous tissue to be excised without inflicting damage on healthy tissue, and it would reduce the possibility of leaving a few cancerous cells behind to cause a recurrent tumor in the patient. And it would at the same time reduce the surgical risk to the patient.

The use of a computer as the control station for the laser focusing mirror would allow the surgeon to prepare simulation and testing programs using software models with the computer to run test scenarios before the laser is actually used on the patient. These test scenarios could be run on inert models or run on the patient in vivo by using the helium-neon pilot steering beam of the $CO_2$ laser, before the actual cutting beam is turned on.

This would give the surgeon an immediate, direct outline of how the procedure is to be executed on the patient. In this way the surgeon could conduct a pre-evaluation and first test whether or not the program covered all the necessary points. When the surgeon is satisfied by this test procedure that the program is complete, he may then run the program and permit the computer to perform the surgery under his direction and control.

Software modeling can save a great deal of time in the operating room and give surgeons the ability to stay current and in practice so that they do not lose their "touch" with the laser. Such computer simulations using the laser focusing mirror are also useful in medical education.

While there has been shown and described a preferred embodiment of LASER BEAM SURGICAL SYSTEM in accordance with the invention, it will be appreciated that many changes and modifications may be made therein without, however, departing from the essential spirit thereof.

I claim:

1. A steerable laser beam system for performing surgery at a target in a surgical site within a body cavity, said system comprising:
   A. a cannula insertable into a body passage leading to the surgical site, said cannula including a rotatable inner tube provided with an inlet section having an input port and an outlet section provided with a lateral output port which, by rotation of the inner tube, can be made to assume a position adjacent the target;
   B. a laser source coupled to said input port to produce a collimated laser beam which is directed toward said outlet section;
   C. a normally planar deformable membrane having a reflective surface supported in said outlet section at an angle with respect to the inner tube axis to project the laser beam impinging thereon through said output port toward the target in the surgical site; and
   D. a controllable actuator coupled to the rear of the membrane at its geometric center to force said membrane to assume a concave form having a quasi-parabolic shape which optically brings said beam to a focus at the surgical site target, so that by rotating the inner tube and by focusing the beam projected from said output port one can steer the beam to precisely strike the target; said membrane having an elliptical form and being peripherally joined by an elastomeric coupler to a rigid supporting ring so that the membrane, when it is deformed to assume a quasi-parabolic shape, is not distorted at its periphery.

2. A system as set forth in claim 1 wherein said membrane is formed of a material having a reflective aluminized surface.

3. A system as set forth in claim 1 wherein said membrane is formed of a titanium plate having a reflective polished surface.

4. A system as set forth in claim 1 where the cross-sectional dimension of said membrane is relatively thin at its geometric center and becomes increasingly thick as one moves away from this center.

5. A system as set forth in claim 1 wherein said inlet section is provided with a first input port in line with the axis of the inner tube and a second input port at right angles thereto, and a pellicle supported in the inlet section at 45° to said axis which is transparent to white light and reflective to said laser beam, the laser being coupled to said second input port and a source of white light being coupled to said first input port whereby both the white light and laser beam are directed toward the outlet section to be reflected by the membrane, the white light illuminating the surgical site.

6. A system as set forth in claim 1 wherein said inner tube is coaxially disposed within an outer tube and is rotatable therein, whereby the laser beam projected from the membrane and focused thereby may be steered within a sector determined by the output port.

7. A system as set forth in claim 1 further including a source of helium gas and means to introduce said gas into the input port of the inner tube so that it is discharged from the output port into the surgical site to effect inflation thereof.

8. A system as set forth in claim 1 wherein said actuator is an electrically-operated element which is coupled to the rear of the membrane through a drive pin.

9. A system as set forth in claim 8 wherein said element is a piezoelectric element which is adapted to displace the pin in either of two directions.

10. A system as set forth in claim 5 further including a lens system to optically couple said pellicle to a video camera whereby the illuminated surgical site may be viewed in a television camera.

11. A system as set forth in claim 1 wherein said beam is a $CO_2$ laser beam.

12. A system as set forth in claim 1 wherein said beam is an Argon laser beam.

13. A system as set forth in claim 1 wherein said beam is formed by a bundle of laser beams of different wavelengths.

* * * * *